United States Patent [19]
Kannourakis

[11] Patent Number: 5,599,789
[45] Date of Patent: Feb. 4, 1997

[54] METHOD FOR THE TREATMENT OF TUMOURS AND SARCOMAS

[75] Inventor: George Kannourakis, Mt. Clear, Australia

[73] Assignee: Amrad Corporation Limited, Victoria, Australia

[21] Appl. No.: 107,767

[22] PCT Filed: Dec. 24, 1992

[86] PCT No.: PCT/AU92/00683

§ 371 Date: Aug. 24, 1993

§ 102(e) Date: Aug. 24, 1993

[87] PCT Pub. No.: WO93/12806

PCT Pub. Date: Jul. 8, 1993

[30] Foreign Application Priority Data

Dec. 24, 1991 [AU] Australia .................................. PL0164

[51] Int. Cl.⁶ .................................................. A61K 38/16
[52] U.S. Cl. .................................................................. 514/8
[58] Field of Search ........................................................ 514/8

[56] References Cited

U.S. PATENT DOCUMENTS 5,187,077  2/1993  Gearing et al. ..................... 435/69.1

FOREIGN PATENT DOCUMENTS

90/00556  11/1990  WIPO .
90/00592  12/1990  WIPO .
91/00103  3/1991   WIPO .

*Primary Examiner*—Jerome D. Goldberg
*Attorney, Agent, or Firm*—Scully, Scott, Murphy & Presser

[57] ABSTRACT

The present invention relates to the use of leukaemia inhibitory factor and pharmaceutial compositions comprising same in the treatment of undifferentiated tumours and sarcomas in mammals.

11 Claims, 11 Drawing Sheets

METHOD FOR THE TREATMENT OF TUMOURS AND SARCOMAS

This application is a 371 of PCT/AU92/00683 filed Dec. 24, 1992.

The present invention relates generally to the use of leukaemia inhibitory factor and pharmaceutical compositions comprising same in the treatment of undifferentiated tumours and sarcomas in mammals. The present invention is particularly directed to the treatment of Ewing's Sarcoma, Rhabdosarcoma and other sarcomas of connective tissue, bones, bladder, kidneys, liver, lungs, parotids or spleen.

Leukaemia inhibitory factor (hereinafter referred to as "LIF") was purified (1,2) and cloned (3) on the basis of its capacity to induce differentiation in and suppress the M1 mouse myeloid leukaemic cell line (see International Patent Application No. PCT/AU88/00093) and has been shown to possess a variety of actions: it releases calcium from bone tissues (5), is the factor preventing spontaneous differentiation in normal embryonic stem cells (6,7), is a molecule stimulating DA1 cell proliferation (4), stimulates liver cells to produce acute phase proteins (8,9), and is a lipoprotein lipase inhibitor (10).

The present invention arose in part from an investigation of the effect of LIF on Ewing's Sarcoma, the second most common malignant bone tumour of children and young adults, accounting for approximately 7% of all malignant tumours of bone. The predominant localisation of these tumours is in the metaphyses of long bone and the pelvic region, although the extremities, ribs and spine or any other bone may be affected and they can also metastise to the lungs.

Macroscopically, the tumours are a jelly-like mass with foci of haemorrhage on their cut surface. Microscopically, they are made up of sheets of densely packed, undifferentiated, small round cells, divided into small groups or nests by fibrous-tissue septa.

With current treatment, patients with small localised tumours have an approximately 50% chance of survival, however, those with large or metastatic tumours have a poor prognosis (12). Recent studies have demonstrated that Ewing's Sarcoma cells have the capacity to undergo differentiation into neural cells, suggesting that the precursor cell for this tumour originates from the neural lineage (13). The cytogenetic study of these tumours has revealed that the majority are associated with a t(11:22) translocation (14). At present the molecular basis of this translocation remains unknown, and although a number of candidate oncogenes located close to the translocation have been extensively studied, none have been found to be involved in Ewing's Sarcoma (including C-sis, c-ets, proto-oncogenes). Furthermore, to date only a few Ewing's Sarcoma cell lines have been reported (15,16).

In work leading to the present invention, the effects of various growth factors on the proliferation of sarcoma cell lines were studied. In accordance with the present invention, it has been surprisingly discovered that LIF can cause a significant reduction in tumour size indicating its potential as an anti-tumour agent in the treatment of undifferentiated tumours and sarcomas.

Accordingly, one aspect of the present invention contemplates a method for the treatment of mammals carrying undifferentiated tumours and/or sarcomas which method comprises administering to said mammal an effective amount of LIF and/or active fragments or derivatives thereof for a time and under conditions sufficient to destroy or reduce the size of undifferentiated tumours and/or sarcomas.

Another aspect of the present invention further comprises the simultaneous or sequential administration of one or more other cytokines, derivatives thereof and/or one or more chemotherapeutic agents and/or the simultaneous or sequential treatment by radiotherapy. By "simultaneous or sequential" is meant that LIF is co-administered with another cytokine or chemotherapeutic agent or together with radiotherapy or where LIF administration is preceded or followed by non-LIF treatment. Where "sequential" therapy is occurring, the time difference between LIF administration and non-LIF treatment may be minutes, hours, days, weeks or months depending on the tumour or sarcoma being treated, the mammal being treated and the effectiveness of the overall treatment.

The present invention is exemplified by the effect of LIF in vitro and in vivo against Ewing's Sarcoma cells. This is done, however, with the understanding that the present invention extends to the in vivo effects of LIF in all meals such as humans, livestock animals and companion animals and in particular humans and to all undifferentiated tumours and sarcomas.

Preferably, the mammalian LIF is of human, murine or livestock origin, companion animal, laboratory test animal or captive wild animal. More preferably, it is of human or murine origin and most preferably it is of human origin provided that the LIF has the desired activity herein described. In this regard, the LIEF employed may be "homologous" to the mammal to be treated meaning that it has the same origin as the species of mammal to be treated (e.g. human LIF for treatment of a human or murine LIF for treatment of a mouse) or may be "heterologous" to the mammal to be treated meaning that the species origin of LIF and the species of the mammal are different (e.g. human LIF for treatment of a mouse or murine LIF for treatment of a human).

The active ingredients may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thirmerosai and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected as described above, the composition may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound(s) in the pharmaceutical compositions is such that a suitable dosage will be obtained. Preferred compositions or preparations according to the present invention are prepared, so that an oral dosage unit form contains between about 0.5 ng and 20 mg of active compound.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carriers and/or diluents" include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated. Supplementary active ingredients can also be incorporated into the compositions.

The present invention further relates to the use of LIF or active fragment, mutant or derivative thereof alone or together with one or more other cytokines and/or chemotherapeutic agents in the manufacture of a medicament for the treatment of patients carrying tumours or sarcomas such as Ewing's Sarcoma, Rhabdosarcoma and other sarcomas of connective tissue, bones, bladder, kidneys, liver, lings, parotids or spleen.

A livestock animal includes cows, pigs, sheep, horses and goats. A companion animal includes cats and dogs. A laboratory test animal includes mice, rabbits, guinea pigs, hamsters and poultry birds such as chickens. A captive wild animal includes emus, foxes, kangaroos and wild birds.

The LIF employed is preferably in recombinant form as described in International Patent Application No. PCT/AU88/00093. Preferably, the LIF comprises an amino acid sequence set forth in one or more of the Figures in PCT/AU88/00093 or is substantially similar thereto. In its most preferred form, the LIF has the amino acid sequence set forth in FIGS. 15, 26 or 29 of PCT/AU88/00093 or has an amino acid sequence with at least 40%, more preferably at least 50%, even more preferably at least 60%, still more preferably at least 70–80% and yet even more preferably at least 90–95%, similarity or identity to at least one region of the amino acid sequence set forth in FIGS. 15, 26 or 29 of PCT/AU88/00093. The LIF may also contain single or multiple amino acid insertions, deletions and/or additions to the naturally occurring sequence and may be derivatised or fragmentised to a part carrying the active site of LIF. All such derivatised or fragmentised LIF molecules are encompassed by the present invention and are included in the expression "LIF", provided all such molecules have the effect of destroying or reducing the size of undifferentiated tumours and/or sarcomas in vitro, in a laboratory test animal in vivo or in a mammal to be treated.

Administration may be by any suitable route such as intravenous, intranasal, subcuteneous, intraperetoneal, intramuscular, intradermal, infusion, suppository, inplant and oral including slow release capsule. However, since LIF has a short serum half-life, the injected preparation may have to be modified to reduce serum degradation and/or the route of administration may need to be altered. Administration may also be by gene therapy including expression of the LIF gene in viral vectors which are introduced to the mammal to be treated. Alternatively, the LIF gene can be expressed in bacteria which are then incorporated into the normal flora of the host.

In accordance with the present invention, it has been discovered that LIF significantly reduces the number of colonies grown in a culture of Ewing's Sarcoma cells as compared to untreated controls, which effect could be demonstrated to be dose-dependent. The magnitude of the colony reduction induced by LIF was greater than those induced by other growth factors tested including Interleukins 1, 3, 4 and 6, M-CSF, G-CSF, GM-CSF, SCF, TNF-$\alpha$, TGF-$\beta$, EGF, acidic and basic FGF, NGF, IGF-1, IGF-11, PDGF and Interferon $\gamma$ and furthermore it was demonstrated that Ewing's Sarcoma cells contain a high number of LIF receptors. These results indicate the potential clinical use of LIF to treat undifferentiated tumours and sarcomas.

As LIF appears to have no colony stimulating activity in conventional semisolid cultures of unfractionated mouse marrow cells or purified progenitor cells, and as Ewing's Sarcoma cells do express LIF receptors, the effects of LIF on colony formation of Ewing's Sarcoma cells would represent direct effects possibly in association with some other factors. Furthermore, the effects of LIF described herein are in contrast to the apparent inactivity of LIF on normal haemopoietic cells in vivo.

Although not wishing to limit the present invention to any one hypothesis of mode of action, it is possible that LIF is acting to initially induce tumour and sarcoma cells to divide rapidly as a first step on a pathway of terminal differentiation. If this is the case, then in suspension culture in the presence of LIF, there may be an initial increase in DNA synthesis or an impaired clonogenicity. Regardless of the mode of action, the effect of LIF in vivo and in vitro in semi-solid cultures is to destroy or reduce the size of undifferentiated tumours and sarcomas.

The effective amount of LIF will depend on the mammal and the condition to be treated. For example, amounts ranging from about 0.1 ng/kg body weight/day to about 1000 µg/kg body weight/day are contemplated to be useful in destroying or reducing the size of tumours and sarcomas. More preferably, the effective amount is 1 ng/kg body weight/day to 100 µg/kg body weight/day. Even more preferably, the effective amount is 10 ng/kg body weight/day to 10 µg/kg body weight/day. Such effective amounts may reflect actual administration protocols or may reflect an average of an alternate administration protocol. The protocol may be varied to administer LIF per hour, week or month or in conjunction with chemotherapy, radiotherapy and/or surgery.

The method of the present invention further contemplates the administration of LIF alone or in combination with other cytokines and/or chemotherapeutic agents and/or a radiotherapeutic protocol and/or with surgery. Such cytokines include, but are not limited to, interleukin-1, TNF-α and/or Interferon γ. Chemotherapeutic agents contemplated in the present invention include, but are not limited to, Actinomycin, Etoposide, Adriamycin, Ifosfamide, Daunorubicin, Vincristine, Cyclophosphamide and/or Dactomycin. Amounts of other cytokines will be similar to the effective amounts of LIF. The effective amounts of chemotherapeutic agents will vary depending on the agent. For example, Vincristine can be given at 0.5–2 mg/m$^2$. Cyclophosphamide is generally provided at about 600–3000 mg/m$^2$ in 100 ml/m$^2$N saline over, for example, 30 minutes.

Adriamycin is conveniently provided at 10–60 mg/m$^2$, daily or in 6 hour infusions in 5% w/v Dextrose. Actinomycin can be provided at 200–1200 µg/m$^2$ daily. Where radiotherapy is employed, radiation dose may be approximately 20–80 gy in 10–40 increments at 1–10 per week depending on the tumour or sarcoma and the mammal to be treated.

In all of the above cases, the present invention also extends to the use of derivatives of LIF and derivatives of other cytokines and/or chemotherapeutic agents. By "derivative" is meant recombinant, chemical or other synthetic forms of LIF or other cytokine or chemotherapeutic agent and/or any alteration such as addition, substitution and/or deletion to the amino acid sequence component of the molecule or to the carbohydrate or other associated molecule moiety of LIF or other cytokine, provided the derivative possesses the ability to destroy and/or reduce the size of undifferentiated tumours. Accordingly, reference herein to "LIF" or to a cytokine or chemotherapeutic agent includes reference to its derivatives. The most preferred form of LIF is human recombinant LIF.

The present invention further extends to pharmaceutical composition comprising LIF and/or its derivatives alone or in combination with one or more other cytokines and/or their derivatives and/or chemotherapeutic agents and one or more pharmaceutically acceptable carriers and/or diluents. Such pharmaceutical compositions will be usehal in the treatment of undifferentiated tumours or sarcomas.

The active ingredients of the pharmaceutical composition comprising the recombinant LIF or routants or fragments or derivatives thereof alone or together with one or more other cytokines and/or chemotherapeutic agents or their derivatives are contemplated to exhibit excellent activity in treating patients with a tumour or sarcoma when administered in an amount which depends on the particular case. Doses may be divided and administered hourly, daily, weekly, monthly or in other suitable time intervals. The active compound may be administered in a convenient manner such as described above. Depending on the route of administration, the active ingredients may be required to be coated in a material to protect same from the action of enzymes, acids and other natural conditions which may inactivate said ingredients. For example, the active ingredients may be destroyed in the gastrointestinal tract by enzymes capable of cleaving peptide bonds and in the stomach by acid hydrolysis. In order to administer the composition by other than parenteral administration, the enzyme will be coated by, or administered with, a material to prevent its inactivation. For example, the active ingredients may be administered in an adjuvant, coadministered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Conveniently, the adjuvant is Freund's Complete or Incomplete Adjuvant. Enzyme inhibitors include pancreatic trypsin inhibitor, diisopropyffluorophosphate (DEP) and trasylol. Liposomes include water-in-oil-in-water emulsions as well as conventional liposomes.

The method and pharmaceutical compositions described in accordance with the present invention will be useful in the treatment inter alia of undifferentiated tumours or sarcomas including but not limited to Ewing's Sarcoma, Rhabdosarcoma, and other sarcomas of connective tissue, bones, bladder, kidneys, liver, lungs parotid or spleen.

The present invention is further described by reference to the following non-limiting Figures and Examples.

Figure 5A:
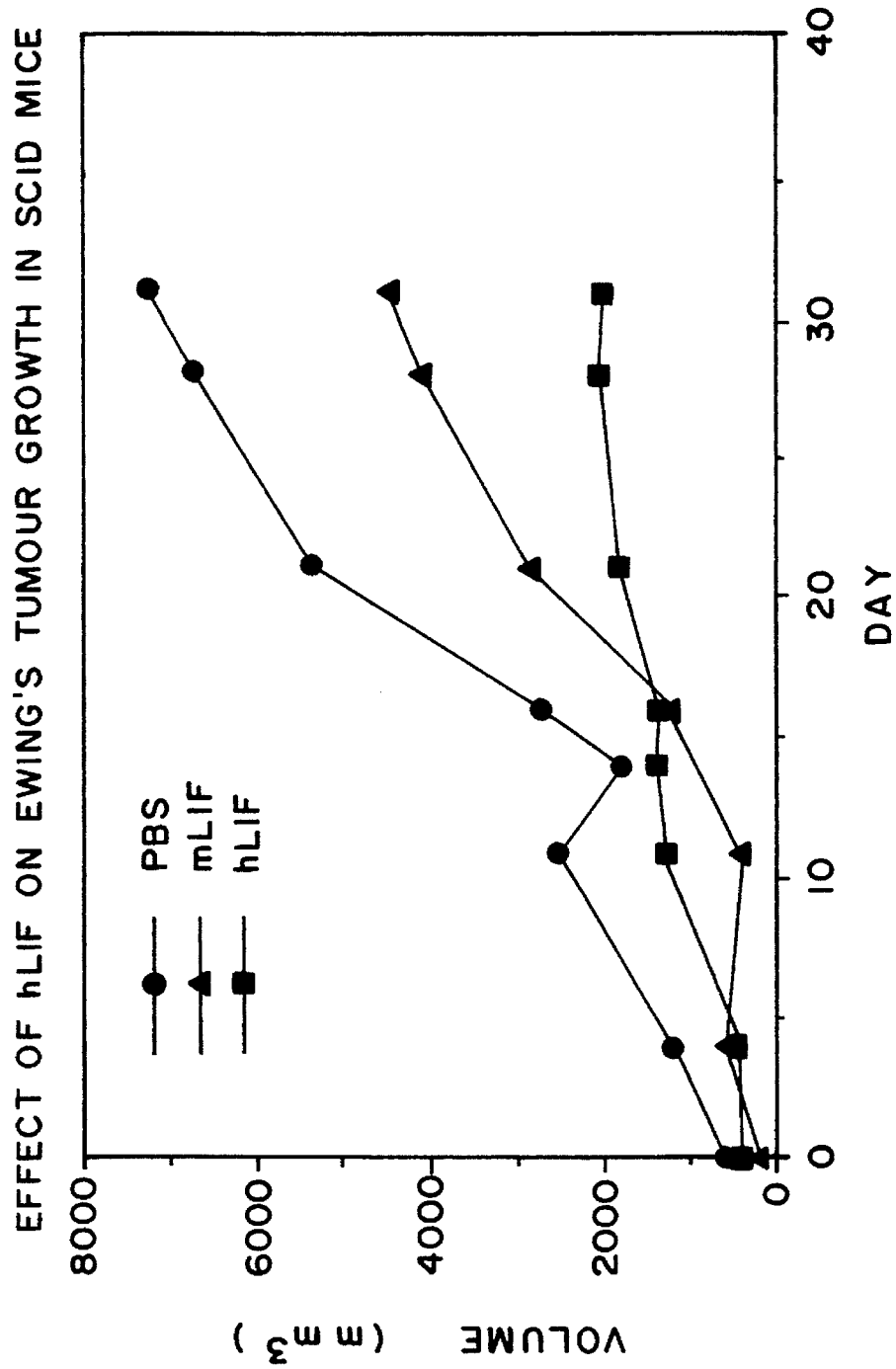
Figure 5B:
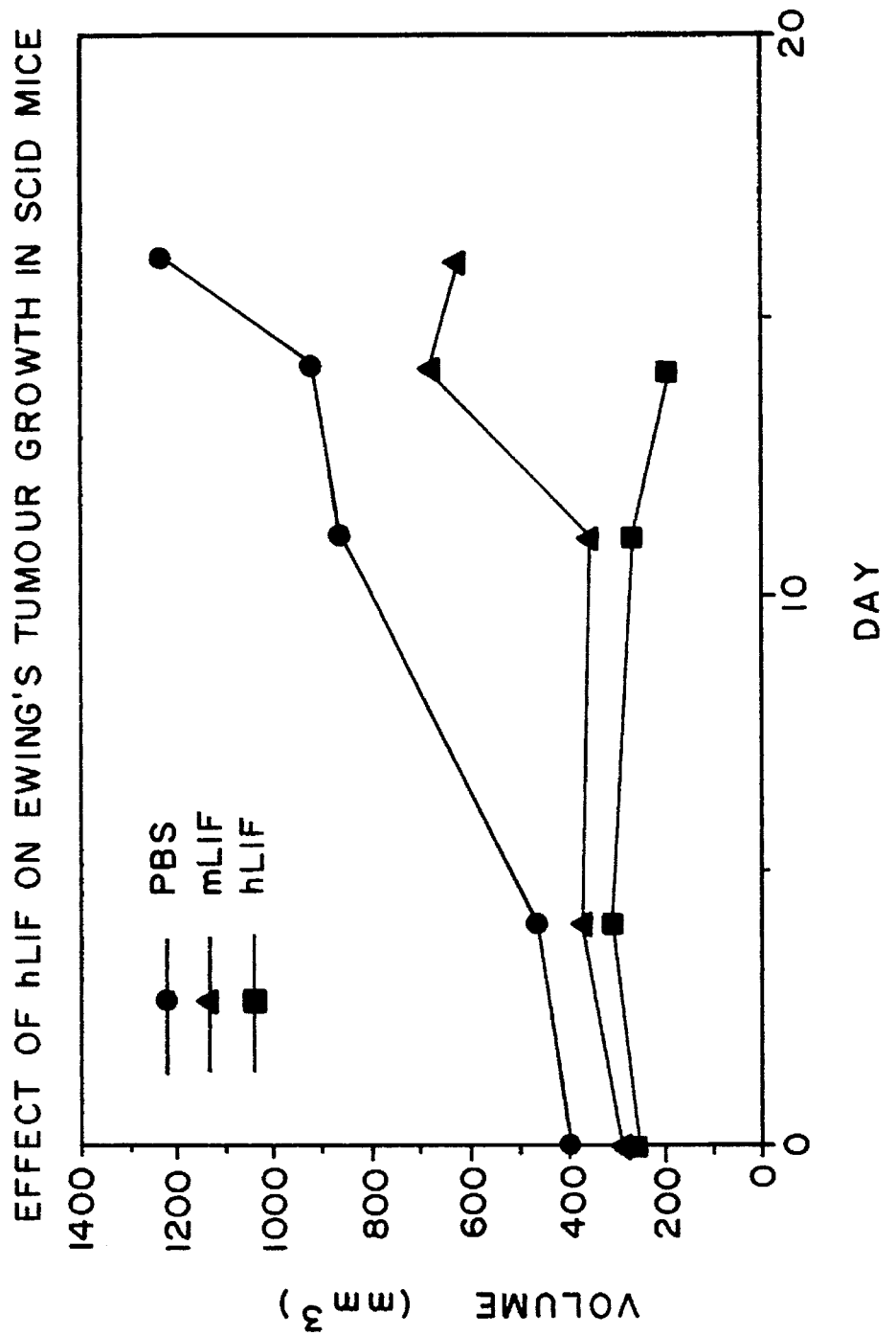
Figure 5C:
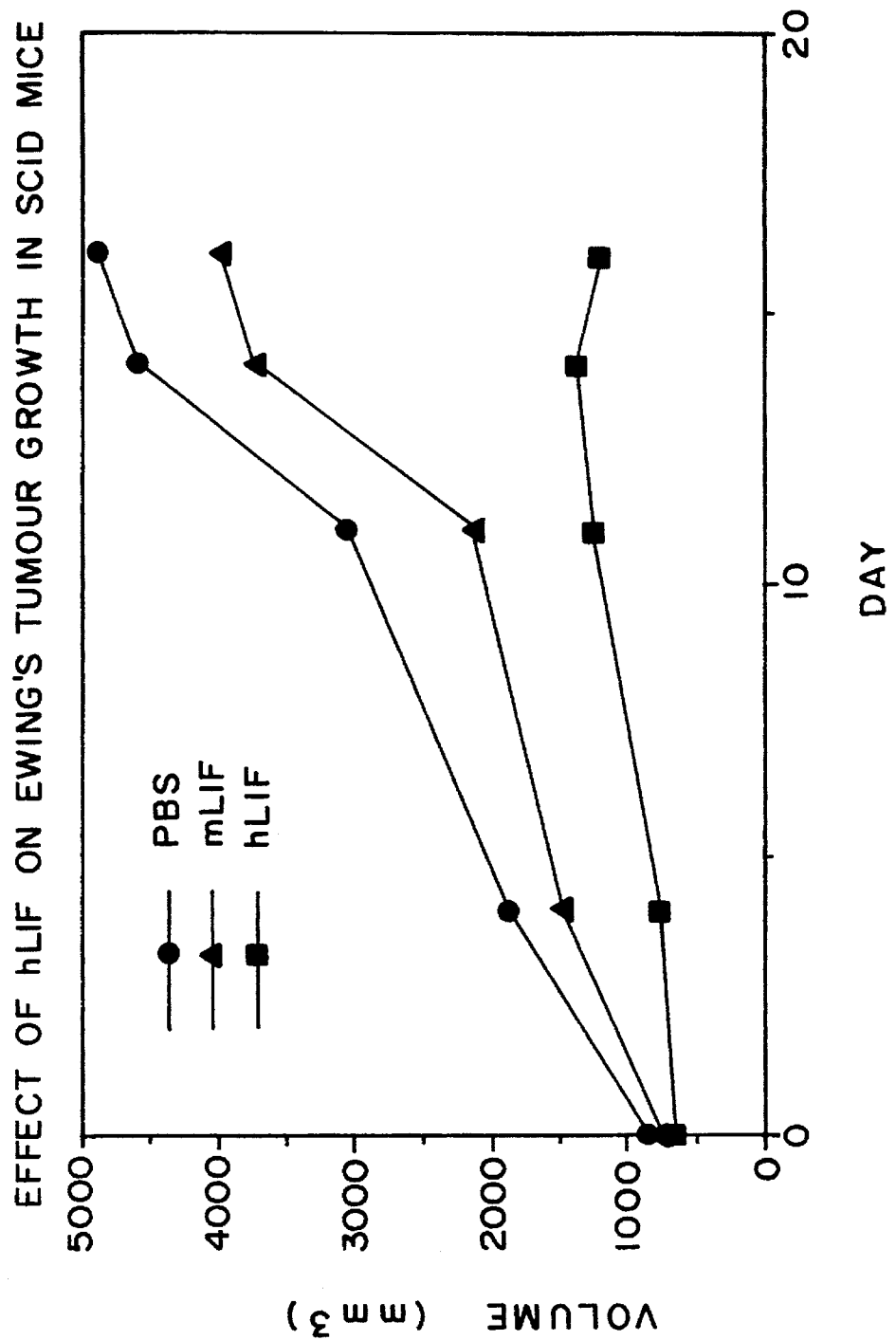

FIGS. 5A, B & C are graphical representations showing the effect of LIF on Ewing's tumour growth in SCID mice that were grouped according to initial tumour size ranges. FIGS. 5A and 5B show the effects of ●PBS, ▲mLIF or ■hLIF on tumour growth in mice which initially had medium size tumours; in FIG. 5C, the mice initially had large size tumours.

FIGS. 6A–D are photographic representations showing:

A: Low power (×40) Magnification of Haematoxylin and Eosin stained subcutaneous Ewing's sarcoma xenograft, taken after 18 days treatment with PBS. Tumour cells have invaded surrounding tissues.

B: Low power (×40) Magification of Haemaxoxylin and Eosin stained subcutaneous Ewing's sarcoma xenograft, taken after 18 days treatment with 20 µg/day human LIF. The diffuse, pale regions, represents regressive, nectrotic tumour cells.

C: High power (×400) Magnification of Haematoxylin and Eosin stained subcutaneous Ewing's sarcoma xenograft, after 18 days of treatment with daily injections of PBS. The dense, round cell bodies with a darkly staining nucleus represent viable aggressive tumour cells with mitotic figures, invading the surrounding subcutaneous and muscle tissue.

Figure 6A:
Figure 6B:
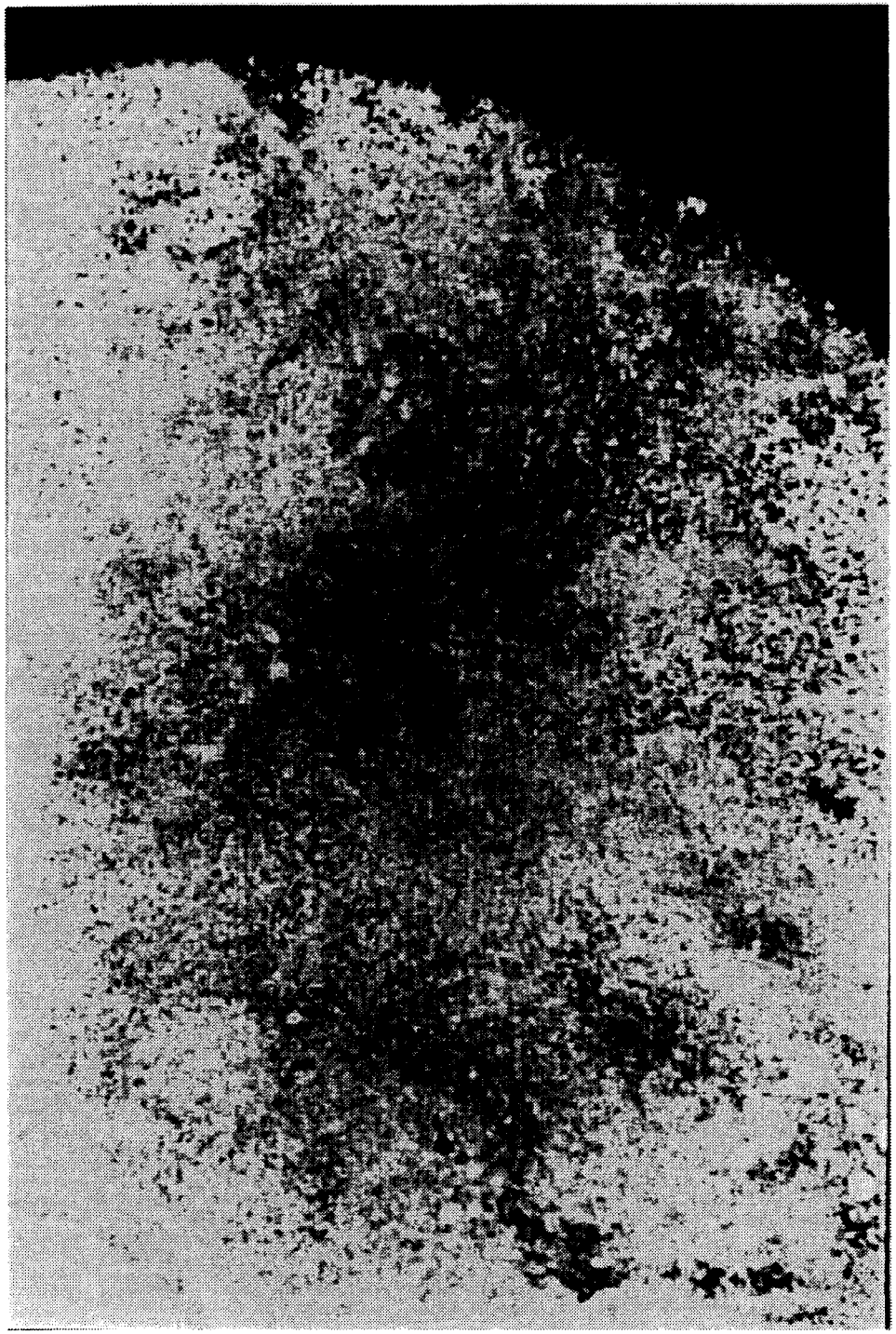
Figure 6C:
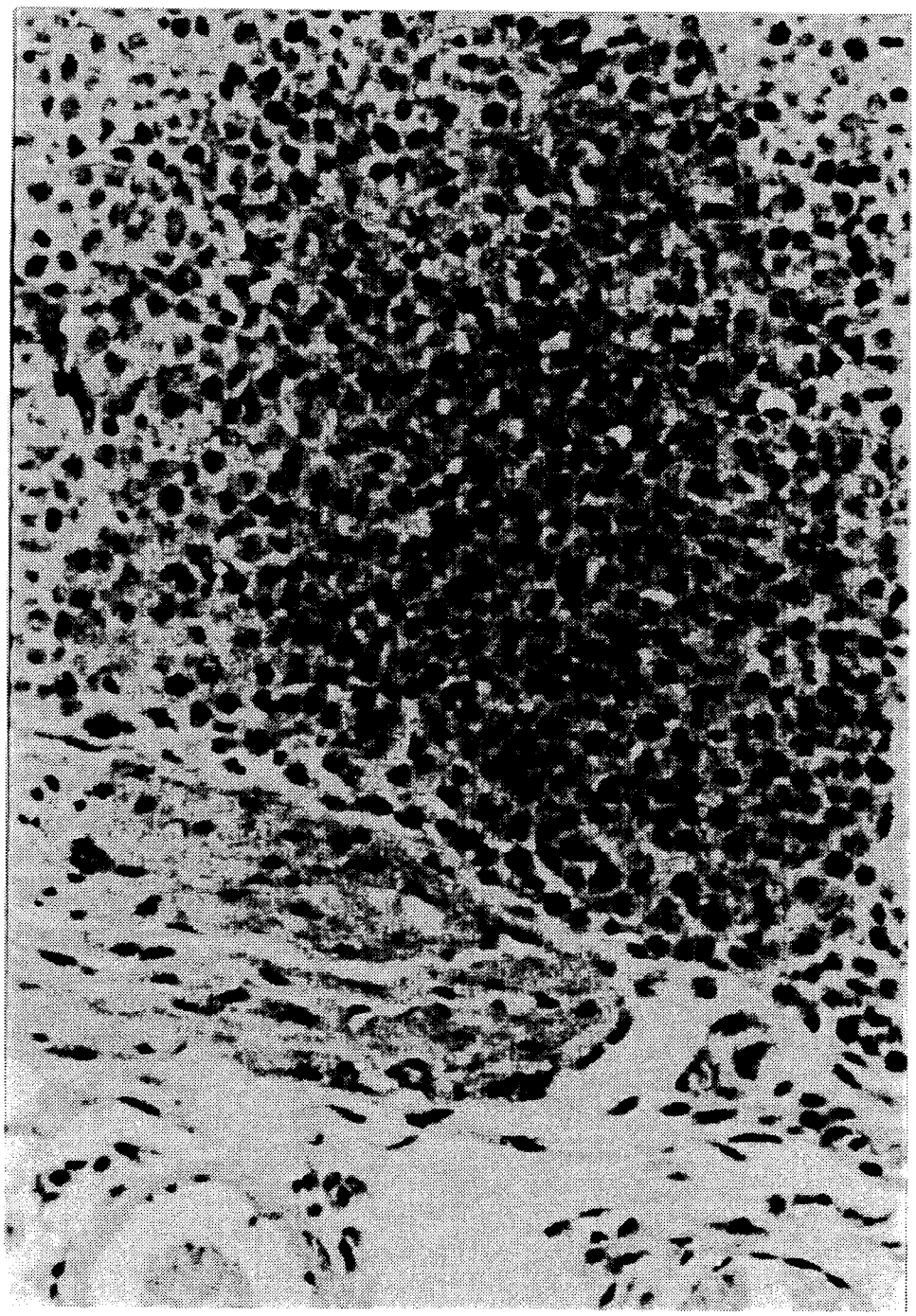
Figure 6D:

D: High power (×400) magnification of Haematoxylin and Eosin stained subcuaneous Ewing's sarcoma xenograft, after 18 days of treatment with human LIF (20 μg/day). The pale regions represent necrotic, regressive tumour cells, distinguished by the lack of mitotic figures as opposed to the high number of mitotic figures observed in the control tumours (FIG. 6C).

EXAMPLE 1

1. Materials and Methods

Cells

Tumour cells obtained from biopsy and bone marrow specimens from patients with Ewing's Sarcoma were used in these studies. Approval for this project has been obtained from the Ethics Committee of the Royal Children's Hospital.

Single cell suspensions of tumour cells were obtained by mechanical disruption with an 18G or 21G needle or by pipetting, followed by incubation with dispase II (Boehringer) at a concentration of 1.2 units per ml for 10 minutes at 37° C. Prior to the addition to agar-medium the cells were vortexed gently to prevent clumping.

Clonal cell lines were grown in Iscove's Modified Dulbecco's Medium (IMDM) supplemented with 10% v/v foetal calf serum (FCS; CSL Limited, Melbourne, Australia) and were passaged either weekly or twice weekly. The characteristics of the Ewing Sarcoma cell lines used herein as described below:

| Tumour | Specimen | Age | Sex | Passage No. | Chrom. |
| --- | --- | --- | --- | --- | --- |
| Al Metastatic | Bone Marrow | 12 | M | >80 | t11:22 |
| Cu Primary | Pelvis | 2 | F | >80 | t11:22 |

Cell lines derived from the above primary cell lines (Al and Cu) are identified by an Arabic numeral (e.g. Al-1, Al-5, Al-8 or Cu-1).

Semi-Solid Cultures

The tumour cells were immobilised in 0.3% w/v agar containing Iscove's Modified Dulbecco's Medium (IMDM) and 10% v/v FCS. LIF as well as other growth factors were added in various concentrations to the 35 mm petri dishes to which 1 ml of cells-agar medium were gently mixed and after gelling at room temperature, the cultures were incubated in a humidified 5% v/v $CO_2$ environment for 12 to 18 days. Cultures were scored for the presence of colonies (>40 cells) or clusters (<40 cells). The number of cells plated per culture ranged from 500 to 10,000 per ml. Colonies were counted on an Olympus dissecting microscope.

Growth Factors

Various commercially available growth factors were used in this study. These included:

IL-1, IL-3, IL-4, IL-6, M-CSF, G-CSF, GM-CSF, Stem Cell Factor (SCF), TNFα, TGFα, TGFβ, EGF, aFGF, bFGF, NGF, IGF I, IGF II, PDGF and IFN-γ.

The recombinant human leukaemia inhibitory factor (LIF) was obtained from AMRAD Corporation Limited, Melbourne, Australia.

2. Effects of LIF and other Growth Factors on Ewing's Cell Lines

Tables 1–3 show the effects of various growth factors and lymphokines on the formation of colonies in agar cultures on a number of different Ewing's cell lines. It was found that LIF at physiological doses of between 0.1 and 100 ng LIF per culture was able to significantly reduce colony counts. None of the other factors, with the exception of TNF-α showed any effect on colony counts. It must be noted, however, that the dose of TNF-α used in these studies was far above the physiological dose.

TABLE 1

| Cells | No of Cells | Stimulus | Colonies/Cultures* |
| --- | --- | --- | --- |
| Al(uncloned) | 5,000 | NIL | 257 |
| | | LIF (100 ng) | 8 |
| | | LIF (10 ng) | 10 |
| | | LIF (1 ng) | 160 |
| | | LIF (0.1 ng) | 205 |
| | | LIF (0.01 ng) | 222 |
| | | IL-1 (100 u) | 200 |
| | | NGF (100 ng) | 165 |
| | | EGF (100 ng) | 258 |
| | | aFGF (100 ng) | 260 |
| | | PDGF (30 ng) | 352 |
| | | SCF (100 ng) | 225 |
| | | TGFa (20 ng) | 190 |
| | | TGFb (5 ng) | 175 |
| | | TNFa (5 ug) | 39 |
| | | IL-4 (1:3000) | 165 |
| Al-5 | 1,000 | NIL | 48 |
| | | LIF (100 ng) | 2 |
| | | LIF (10 ng) | 18 |
| | | LIF (1 ng) | 25 |
| | | LIF (0.1 ng) | 27 |
| | | LIF (0.01 ng) | 47 |
| | | IL-1 (100 u) | 33 |
| | | NGF (100 ng) | 32 |
| | | EGF (100 ng) | c |
| | | aFGF (100 ng) | 58 |
| | | PDGF (30 ng) | 39 |
| | | SCF (100 ng) | 42 |
| | | TGF (100 ng) | 45 |
| | | TGFb (5 ng) | 41 |
| | | TNFa (5 ug) | 0 |
| | | IL-4 (1:3000) | 38 |

*Mean of duplicate colony counts on day 18 of culture.

TABLE 2

| Cells | No of Cells | Stimulus | Colonies/Cultures* |
| --- | --- | --- | --- |
| Al-8 | 1,000 | NIL | 72 |
| | | LIF (100 ng) | 3 |
| | | LIF (10 ng) | 6 |
| | | LIF (1 ng) | 23 |
| | | LIF (0.1 ng) | 29 |
| | | LIF (0.01 ng) | 68 |
| | | IL-1 (100 u) | 56 |
| | | NGF (100 ng) | 52 |
| | | EGF (100 ng) | 68 |
| | | aFGF (100 ng) | 128 |
| | | PDGF (30 ng) | 72 |
| | | SCF (100 ng) | 77 |
| | | TGFa (20 ng) | 87 |
| | | TGFb (5 ng) | 45 |
| | | TNFa (5 ug) | 1 |
| | | IL-4 (1:3000) | 82 |
| Al-1 | 10,000 | NIL | 750 |
| | | LIF (100 ng) | 18 |

TABLE 2-continued

| Cells | No of Cells | Stimulus | Colonies/Cultures* |
|---|---|---|---|
| | | LIF (10 ng) | 17 |
| | | LIF (1 ng) | 129 |
| | | LIF (0.1 ng) | 305 |
| | | LIF (0.01 ng) | 695 |
| | | IL-1 (100 u) | 700 |
| | | NGF (100 ng) | 810 |
| | | EGF (100 ng) | 685 |
| | | aFGF (100 ng) | 975 |
| | | PDGF (30 ng) | c |
| | | SCF (100 ng) | 950 |
| | | TGF (100 ng) | 690 |
| | | TGFb (5 ng) | 540 |
| | | TNFa (5 ug) | 2 |
| | | IL-4 (1:3000) | 720 |

*Mean of duplicate colony counts on day 18 of culture.

TABLE 3

| Cells | No of Cells | Stimulus | Colonies/Cultures* |
|---|---|---|---|
| Cu-1 | 10,000 | NIL | 485 |
| | | LIF (100 ng) | 125 |
| | | LIF (10 ng) | 97 |
| | | LIF (1 ng) | 192 |
| | | LIF (0.1 ng) | 430 |
| | | LIF (0.01 ng) | 542 |
| | | IL-1 (100 u) | 338 |
| | | NGF (100 ng) | 360 |
| | | EGF (100 ng) | 430 |
| | | aFGF (100 ng) | 520 |
| | | PDGF (30 ng) | 390 |
| | | SCF (100 ng) | 440 |
| | | TGFa (20 ng) | 390 |
| | | TGFb (5 ng) | 385 |
| | | TNFa (5 ug) | 190 |
| | | IL-4 (1:3000) | 325 |
| Al-1 | 1,000 | NIL | 70 |
| | | LIF (100 ng) | 32 |
| | | LIF (10 ng) | 24 |
| | | LIF (1 ng) | 23 |
| | | LIF (0.1 ng) | 39 |
| | | LIF (0.01 ng) | 50 |
| | | IL-1 (100 u) | 30 |
| | | NGF (100 ng) | 49 |
| | | EGF (100 ng) | 41 |
| | | aFGF (100 ng) | 57 |
| | | PDGF (30 ng) | 47 |
| | | SCF (100 ng) | 51 |
| | | TGF (100 ng) | 47 |
| | | TGFb (5 ng) | c |
| | | TNFa (5 ug) | c |
| | | IL-4 (1:3000) | 47 |

*Mean of duplicate colony counts on day 18 of culture.

3. Effect of LIF on Ewing's Sarcoma Cells in Agar Cultures

Figure 4:
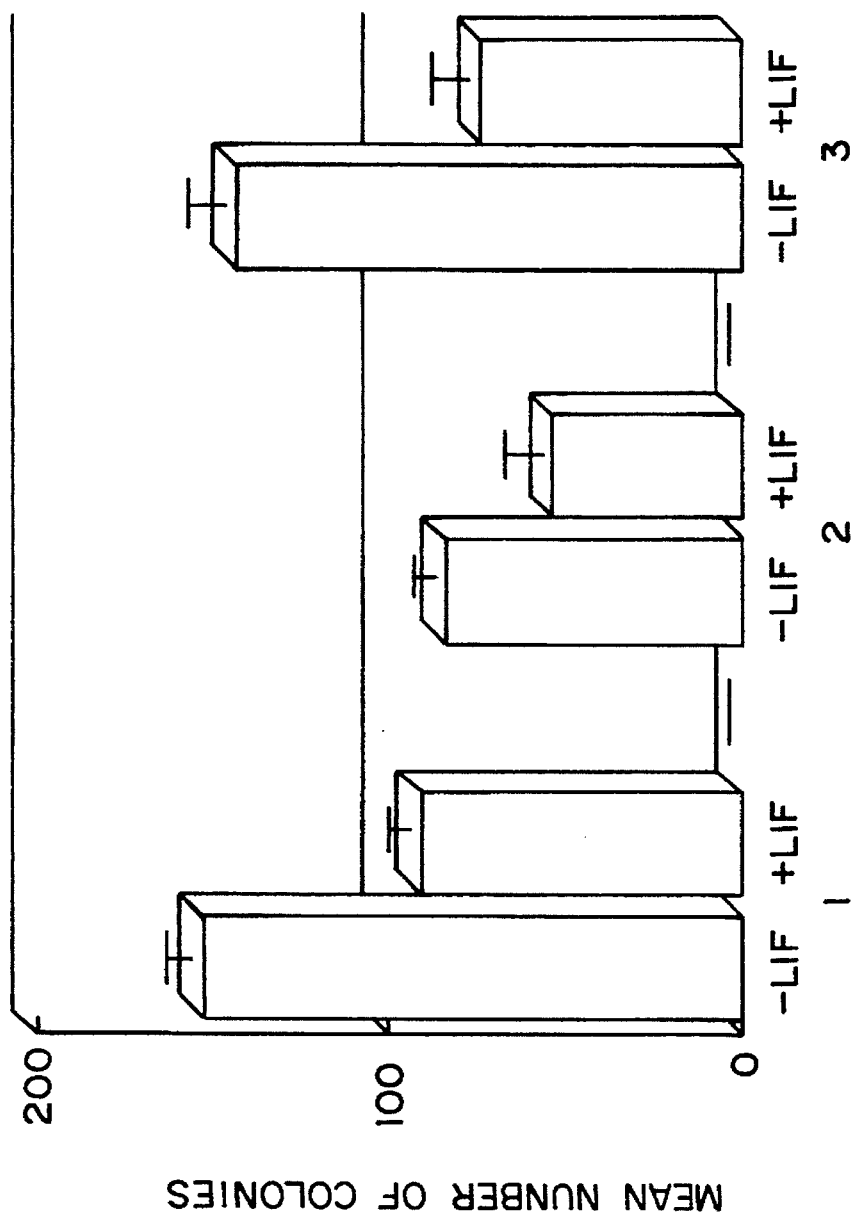
FIG. 4 is a graphical representation showing the effect of LIF on clonogenicity of Ewing's cells in agar culture.

Ewing's sarcoma cells from cell line Al-5 in suspension cultures were incubated for seven days in the presence or absence of 100 ng/ml LIF prior to inoculation of replicate agar plates with 5×10³ cells per ml which were then incubated for a further 18 days before colonies were scored. The results of three separate experiments are shown in FIG. 4. In all cases, the frequency of colonies obtained from LIF-pretreated cells was 35-55% lower compared to control cells. The proportion of large colonies in LIF stimulated agar cultures was further reduced with pretreatment with LIF in suspension cultures for 7-14 days.

EXAMPLE 2

LIF Receptors on Ewing Sarcoma Cells

This example sets out the steps used to document specific high affinity receptors on Ewing's sarcoma cells.

A cloned Ewing sarcoma cell line Al5 (7×10⁶ per point) in 100 µl of RPMI-medium containing 10 mM Hepes buffer pH 7.4 and 10% v/v foetal calf serum were incubated with increasing concentrations of $^{125}$I-hLIF (E. coli derived) (5000–800,000 cpm: 100,000 cpm/ng) with or without 5 µg/ml of unlabelled hLIF for 3 hrs on ice. The incubation mixture was then layered over 180 µl cold foetal calf serum, centrifuged at top speed in an Eppendoff microfuge for 10 sec and the tip of the tube containing the cell pellet cut with a scalpel blade and removed for counting in a gamma counter.

Figure 1:
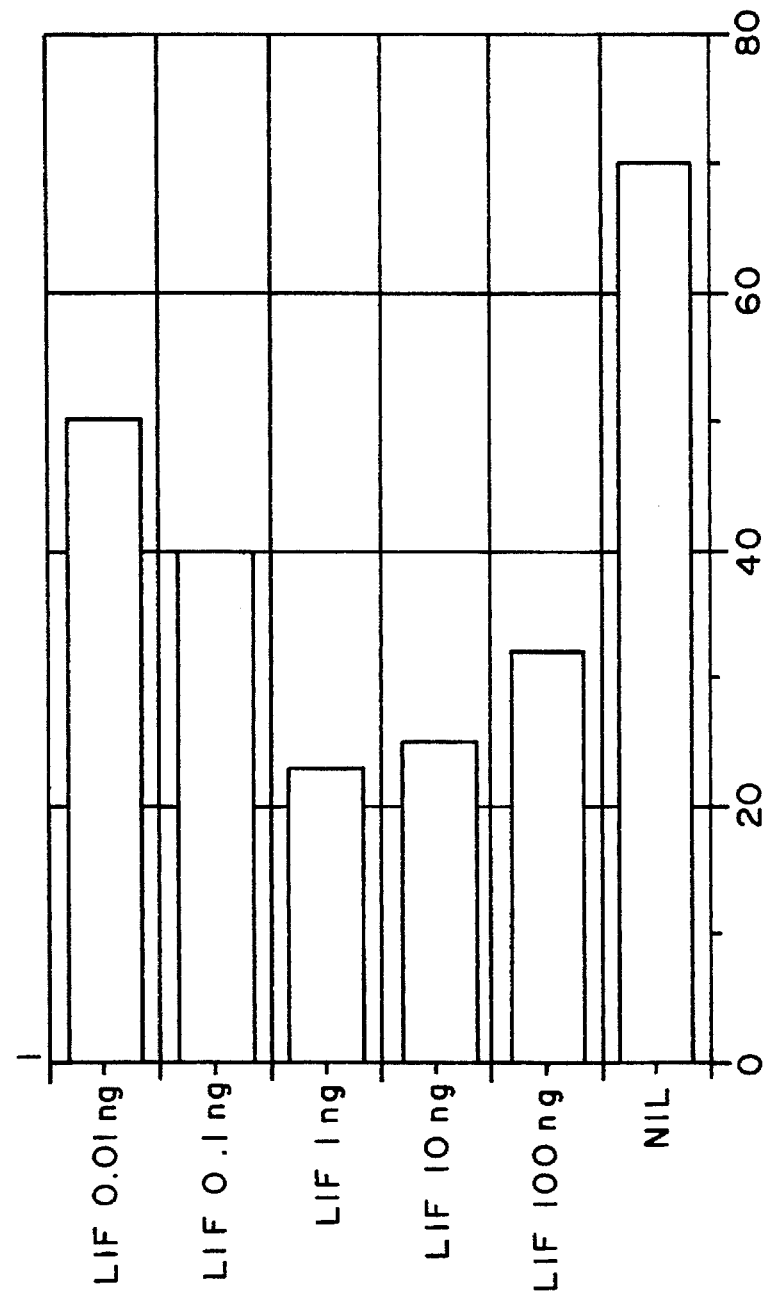
FIG. 1 is a graphical representation showing the dose response effects of LIF, and untreated controls on the undoned Ewing's Sarcoma cell line A4.
Figure 2:
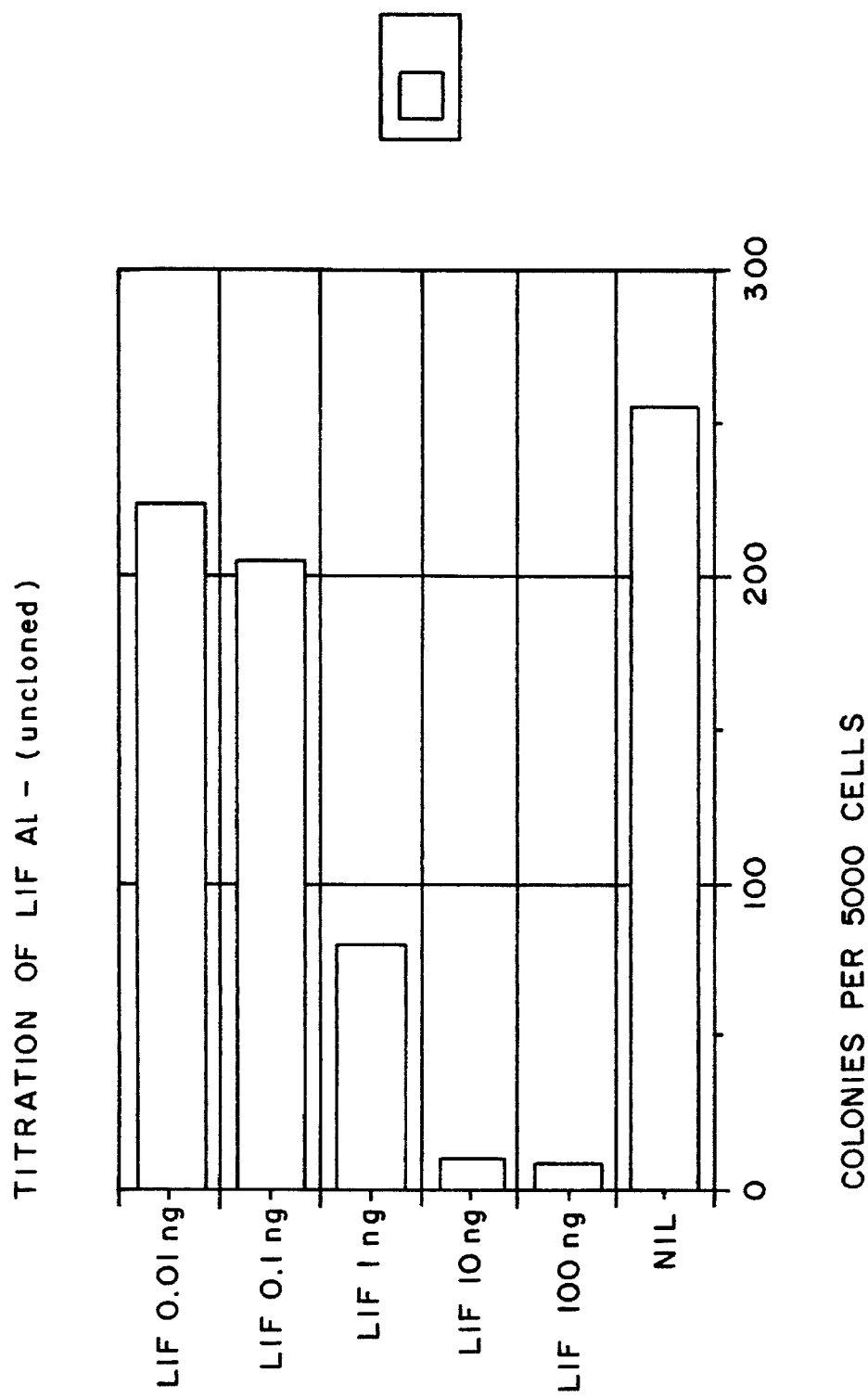
FIG. 2 is a graphical representation showing the dose response effects of LIF and untreated controls, on the cloned Ewing's Sarcoma Cell line AT4.
Figure 3:
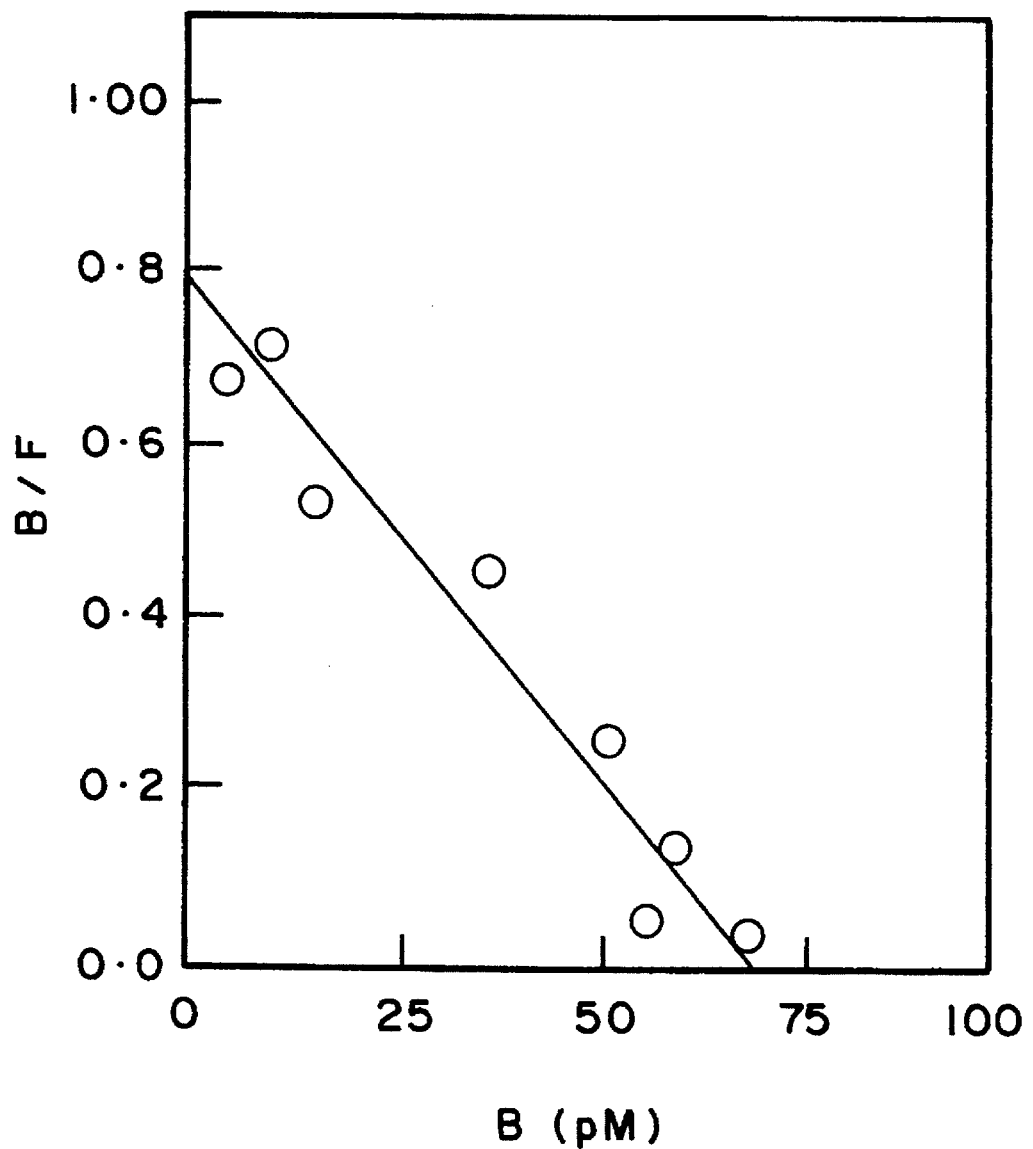
FIG. 3 is a graphical representation showing the binding of $^{125}$I-LIF to Ewing's Sarcoma cell lines.

Scatchard analysis of the binding data (specific bound cpm/free cpm versus specific bound hLIF (pM) is shown in FIG. 3. The slope yielded an equilibrium dissociation constant of 90 pM and the intercept of the abscissa indicated that there were approximately 600 LIF receptors per cell. A second independent Scatchard anlysis of different Ewing sarcoma cells gave an equilibrium dissociation constant of 130 pM and 1000 LIF receptors per cell.

EXAMPLE 3

Effect of Recombinant Human LIF in Mice with Ewing's Sarcoma Tumours

The present Example describes an in vivo model for Ewing's sarcoma using nude and SCID mide, in order to test the effects of LIF on the in vivo growth of Ewing's sarcoma.

1. Materials and Methods

Mice:

Scid mice were obtained from the Animal Resource Centre, Willetton, Western Austarlia. All mice were aged 5–8 weeks, and were the same sex (male). Severe immunodeficiency (scid) is an autosomal recessive mutation that occurred spontaneously in the CB 17 (CB-IgH-1$^b$ (N17F34)) congenic strain (16). In this congenic strain, the inbred BALB/c strain carried the immunoglobulin heavy-chain allele (Igh-I$^b$) of the C57BL/Ka strain. The SCID locus has been mapped to the centromeric end of chromosome 16 (16). These mice have defective T and B cell immunity, thus allowing for engraftment of many foreign cells. The mice were maintained in a laminar flow unit. In order to reduce the mortality from infection, the mice were kept in previously autoclaved cages, and autoclaved food and acidified water was used.

Reagents:

Recombinant human LIF (hLIF) derived from E. coli (Lot 122, AMRAD Corporation Limited) was used. Recombinant mouse LIF (Lot 308, AMRAD Corporation Limited) and PBS/1% w/v BSA were used as controls for the in vivo injections.

Ethics:

This project was approved by the Animal Ethics Committee of the Royal Children's Hospital Research Foundation, Melbourne, Australia.

Method of establishing xenografts:

5–8×10⁶ cloned Ewing's sarcoma cells (cell line A1–5), were injected subcutaneously into SCID mice. Tumours were scored after about 3 weeks in almost all mice at the injection site. Tumour cells were analysed and shown to possess the same starting chromosomal abnormality containing the 11:22 translocation.

2. Results

Toxicity of hLIF

A number of preliminary experiments were performed to determine the appropriate daily dose of hLIF in mice. Mice were injected with high doses of hLIF (100 microgram per mouse). These studies led to death of the mice within 2 weeks of daily subcutaneous injections of LIF. Studies using lower doses (5–20 micrograms per mouse) of hLIF, led to survival of most of the mice for over 20 days. Retro-orbital bleeds were performed on the first 3 days to determine platelet counts. In all mice subcutaneously injected daily with 1 microgram or more of hLIF, the platelet count rose in the first 3 days (26–60% increment on baseline pretreatment levels). In this study an amount of 20 μg of hLIF was chosen to be subcutaneously injected daily into SCID mice bearing Ewing's Sarcoma tumours.

Effect of hLIF on Ewing's Tumour Growth in SCID Mice

To examine the effect of heterologous and homologous LIF relative to the mammal being treated, a double blind controlled study was performed using tumour bearing SCID mice that were injected with hLIF (20 μg per mouse), mouse LIF (100 ng per mouse), or PBS/1% w/v BSA. The effective amount of hLIF was required to be higher than mLIF due to the presence of high circulating levels of a hLIF binding protein in mice (17). Eight mice were injected in each group with the majority of mice in the hLIF group surviving over 2 weeks (range 15–31 days). Tumour size was assessed using calibrated calibers, with measurements in the depth, length and width of the tumours. Mice which had developed similarly size tumours after 3 weeks from xenograft injections were injected with hLIF(■), mLIF (▲), and PBS (●) as shown in FIGS. 5A, B and C. The overall trend observed in FIGS. 5A, B & C was to show that independent of starting tumour size, over time, hLIF and mLIF injected mice had tumours which were significantly reduced in size compared to PBS controls. The trend for smaller tumours in hLIF treated mice was evident prior to the wasting syndrome. Although not wishing to limit the present invention to any one hypothesis as to mode of action, this phenomenon may be a manifestation of LIF toxicity in mice. In most cases, this trend was noticeable within 7 days after hLIF injections.

Histological examination of the subcutaneous tumours was performed on all mice, as was a full necropsy. The results are shown in FIGS. 6A, B, C and D. These studies revealed that Ewing's Sarcoma tumours in hLIF treated mice were mainly composed of necrotic areas with only a small percentage of the tumour being made up of viable cells. The histology of control tumours revealed viable aggressive tumour cells invading the surrounding subcutaneous and muscle tissues. Furthermore, there were almost no mitotic figures observed in the tumours of the hLIF treated mice, which was in stark contrast to the high number of mitotic figures observed in either control tumours.

Accordingly, the results show that the size of tumours in hLIF and mLIF treated mice was significantly smaller compared to PBS treated mice. Examination of the tumours microscopically revealed that hLIF treated tumours had fewer viable areas (<20%) compared to controls (90–100%). The tumour cells in the control mice demonstrated features of malignant cells (high mitotic index, invasiveness of surrounding tissues), whereas the tumours of the hLIF treated mice did not show these features. The studies demonstrate that hLIF and mLIF have a biological effect on growing Ewing's Sarcoma cells in mice, and that these agents will be useful in the treatment of mammals with these types of tumours.

Those skilled in the art will appreciate that the invention described herein is susceptible to variations and modifications other than those specifically described.

It is to be understood that the invention includes all such variations and modifications. The invention also includes all of the steps, features, compositions and compounds referred to or indicated in this specification, individually or collectively, and any and all combinations of any two or more of said steps or features.

REFERENCES:

1. Tomida M., Yamamoto-Yamiguchi Y., Hozumi M., *J. Biol. Chem.* 259: 10978 (1984).
2. Hilton D. J., Nicola N. A., Gough N. M., Metcalf D., *J. Biol. Chem.* 263:9238 (1988).
3. Gearing D. P., Gough N. M., King J. A., Hilton D. J., Nicola N. A., Simpson R. J., Nice E. C., Kelso A., Metcalf D., *EMBO J.* 6:3995 (1987).
4. Moreau J. -F., Donaldson D. D., Bennett F., Witek-Gianotti J. A., Clark S. C., Wong G. G., *Nature* 336:690 (1988).
5. Abe E., Tanaka H., Ishimi Y., Miyaura C., Hayashi T., Nagasawa H., Tomida M., Yamaguchi Y., Hozumi M., Suda T., *Proc. Natl. Acad. Sci. USA* 83: 5958 (1986).
6. Williams R. L., Hilton D. J., Pease S., Willson T. A., Stewart C. L., Gearing D. P., Wagner E. P., Metcalf D., Nicola N. A., Cough N. M., *Nature* 336:684 (1988).
7. Smith A. G., Health J. K., Donaldson D. D., Wong G. G., Moreau J., Stahl M., Rogers D., *Nature* 336:688 (1988).
8. Baumann H., Won K. -A., Jahreis G. P., *J. Biol. Chem.* 264:8046 (1989).
9. Baumann H., Wong G. G, *J. Immunol.* 143:1163 (1989).
10. Mori M., Yamaguchi K., Abe K., *Biochem. Biophys. Res. Commun.* 160: 1085 (1989).
11. Metcalf D., Gearing D. P., *Proc. Natl. Acad. Sci. USA* 86:5948 (1989).
12. Jurgens H., Gobel V., Michaelis J., Ramach W., Rither J., Sauer R., Treuner J., Vonte P. A., Winkler K., Gobel U., *Klin. Paediatr.* 97(3): 225–32 (1985).
13. Cavazzana A. O., Miser J. S., Jefferson J., Triche T. J., *Am. J. Pathol.* 127(3): 507–18 (1987).
14. Aurias A., Rimbault C., Buffe, Duboussef J., Mazabraud A., *C R Seances Acad. Sci.* (III) 296(23): 1105–7 (1983).
15. Lipinkski M., Hirsh M. R., Deagostini-Buzan H., Yamaria O., Tursz T., Goridis C, *Int. J. Cancer* 40(1): 81–6 (1987).
16. Bosma et al *Nature* 301: 527–530, (1983).
17. Layton et al *Proc. Natl. Acad. Sci. USA* 89:8616–8620 (1992).

I claim:

1. A method of treatment of neurally derived undifferentiated tumors in a mammal comprising administering to said mammal an effective amount of leukemia inhibitory factor (LIF) for a time and under conditions sufficient to destroy, or reduce the size of, said neurally derived undifferentiated tumors.

2. The method according to claim 1 wherein said mammal is a human, livestock animal or companion animal.

3. The method according to claim 2 wherein the mammal is a human.

4. The method according to claim 1 wherein the tumour is Ewing's Sarcoma.

5. The method according to claim 1 wherein the LIF is homologous to the mammal to be treated.

6. The method according to claim 1 wherein the LIF is heterologous to the mammal to be treated.

7. The method according to claim 1 wherein the LIF is of human, murine, or livestock animal origin.

8. The method according to claim 7 wherein the LIF is in recombinant form.

9. The method according to claim 1 wherein the effective amount of LIF is from about 0.1 ng per kg body weight per day to about 1000 μg per kg body weight per day.

10. The method according to claim 9 wherein the effective amount is from about 1 ng per kg body weight per day to about 100 μg per kg body weight per day.

11. The method according to claim 9 wherein the effective amount is from 10 ng per kg body weight per day to about 10 μg kg body weight per day.

* * * * *